United States Patent
Lagunas-Solar et al.

(10) Patent No.: US 6,329,136 B1
(45) Date of Patent: Dec. 11, 2001

(54) METHOD FOR LASER INACTIVATION OF INFECTIOUS AGENTS

(75) Inventors: Manuel C. Lagunas-Solar; Bennie I. Osburn, both of Davis; James S. Cullor, Woodland, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/417,986

(22) Filed: Oct. 13, 1999

Related U.S. Application Data (60) Provisional application No. 60/106,198, filed on Oct. 30, 1998.

(51) Int. Cl.[7] .............................. A01N 1/02; C12N 7/04
(52) U.S. Cl. ................................................... 435/2
(58) Field of Search ........................................ 435/2, 236

(56) References Cited

U.S. PATENT DOCUMENTS

| | | |
|---|---|---|
| 2,784,286 | 3/1957 | Dillon . |
| 2,856,505 | 10/1958 | Dillon . |
| 3,443,051 | 5/1969 | Puschner . |
| 3,499,437 | 3/1970 | Balamuth . |
| 3,753,651 | 8/1973 | Boucher . |
| 3,817,703 | 6/1974 | Atwood . |
| 3,926,556 | 12/1975 | Boucher . |
| 3,941,670 | 3/1976 | Pratt, Jr. . |
| 3,955,921 | 5/1976 | Tensmeyer . |
| 4,042,325 | 8/1977 | Tensmeyer . |
| 4,092,800 | 6/1978 | Wayland, Jr. et al. . |
| 4,201,916 | 5/1980 | Ellner . |
| 4,529,489 | 7/1985 | McDonald et al. . |
| 4,590,348 | 5/1986 | Lahti et al. . |
| 4,661,264 | 4/1987 | Goudy, Jr. . |
| 4,758,318 | 7/1988 | Yoshida . |
| 4,871,559 | 10/1989 | Dunn et al. . |
| 4,880,512 | 11/1989 | Cornelius et al. . |
| 5,034,235 | 7/1991 | Dunn et al. . |
| 5,059,431 | 10/1991 | Daeschel et al. . |
| 5,060,414 | 10/1991 | Wayland . |
| 5,089,384 | 2/1992 | Hale . |
| 5,105,563 | 4/1992 | Fingerson et al. . |
| 5,120,450 | 6/1992 | Stanley, Jr. . |
| 5,141,059 | 8/1992 | Marsh . |
| 5,144,146 | 9/1992 | Wekhof . |
| 5,235,043 | 8/1993 | Collins et al. . |
| 5,364,645 | 11/1994 | Lagunas-Solar et al. . |
| 5,607,711 | 3/1997 | Lagunas-Solar . |

FOREIGN PATENT DOCUMENTS

WO 94/28120    12/1994    (WO) .

OTHER PUBLICATIONS

Prodouz et al. Effects of two viral inactivation methods on platelets: laser–UV radiation and merocyanine 540–mediated photoinactivation. Blood Cells. 1992. vol. 18, No. 1, pp. 101–116.

Prodouz et al. Use of laser–UV for inactivation of virus in blood products. Aug. 1987, vol. 70, No. 2, pp. 589–592.

*Primary Examiner*—Sandra Saucier
(74) *Attorney, Agent, or Firm*—John P. O'Banion (57) ABSTRACT

Methods of inactivating pathogens in biological materials, and biological materials that have been so treated, are provided. The inactivation methodology employs UV radiation, by devices such as lasers, to cause inactivation of pathogens, such as viruses.

8 Claims, 3 Drawing Sheets

METHOD FOR LASER INACTIVATION OF INFECTIOUS AGENTS

CROSS-REFERENCE TO RELATED APPLICATIONS

This application claims priority from U.S. provisional application Ser. No. 60/106,198 filed on Oct. 30, 1998.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

The present invention relates to the use of lasers to mediate inactivation of infectious agents, such as viruses, bacteria, fungi and protozoans.

2. Description of the Background Art

There are a variety of viral inactivation approaches known in the art. For example, heat treatments and organic solvents have been used to conduct viral inactivation. There are drawbacks, however. The treatments can denature or inactivate the important biologically active substances, such as a blood proteins. Additionally, the use of substances like organic solvents can result in toxicity problems, and therefore such substances must be removed during the pharmaceutical finishing process.

As an alternative, light-based inactivation approaches have been proposed and are now achievable. Certain approaches rely on ultraviolet light.

The use of ultraviolet light began in the early part of the 20th century when it was recognized that mercury-based UV lamps had a germicidal effect on surface microorganisms. Commercially available UV technology has evolved and has resulted in a widespread use of UV light technology for a variety of commercial applications based upon new generations of reliable, higher power UV lamps.

For example, U.S. Pat. No. 5,364,645 discloses the use of monochromatic low energy pulsed ultraviolet laser irradiation with pulse duration in the range of picoseconds to microseconds at 1–1900 mJ/cm$^2$ to inactivate microorganisms in food. This patent, however, has no applicability to the production of pharmaceuticals, particularly those based upon and/or containing proteins.

U.S. Pat. No. 4,880,512 concerns biological media such as blood fractions, plasma or genetically engineered protein products, that are treated to inactivate viruses. The proteins are kept substantially intact. According to example 2 of the patent, plasma is treated at 258 nm with a flux of $10^{15}$ photons/cm$^2$ using mercury lamp technology. The bacteriophage T4 titer was reduced by $10^6$ while the protein activity has remained at 65% of its original value. According to example 3, 90% of the plasma protein activity remained after a flux of $10^{17}$ photons/cm$^2$. In example 4, the treatment of factor VIII with $10^{14}$ photons/cm$^2$ to inactivate T7 by a factor of $10^6$ is described and a remaining protein activity of 98%. However, the technique employed was a combined ultraviolet and visible light treatment. Additionally, flux of $10^{17}$ photons/cm$^2$ corresponds to a high energy level of about 800 J/cm$^2$.

U.S. Pat. No. 4,871,559 concerns food products that are preserved by inactivating microorganisms and/or enzymes by applying pulses of near visible light. The inactivation of enzymes, however, means that the approach in the '559 patent would deleteriously affect proteins.

WO 94/28120 concerns improving irradiation treatments by using ultraviolet light additives to quench to photodynamic reactions. For example, factor VIII recovery is increased in the presence of a quencher, such as unsaturated fatty acids, reduced sugars and indole derivatives. According to example 11, factor VIII recovery after ultraviolet irradiation was less than 50% in the absence of added quenchers. This publication, however, teaches reliance on the addition of substances like quenchers, which can interfere with the inactivation process.

Although not bound by any theory, it is thought that UV-mediated inactivation occurs through the structural changes it imparts to polynucleotides, such as those found in the genome of the pathogen. For example, UV radiation can cause the formation of thymine dimers between adjacent thymine molecules found in the genome. The formation of thymine dimers can prevent the replication of DNA. UV also can deleteriously impact DNA and RNA by causing hydration of pyrimidine bases.

Despite the above effects, the art still does not accomplish an effective and efficient laser-mediated inactivation approach. Methodologies that result in high viral titer inactivation require high energy and often denature the proteins found in solution. To minimize denaturation, substances like protein stabilizers (such as amino acids) and quenchers can be added, but these substances can decrease the level of inactivation. To increase the efficacy of inactivation while using lower energy levels, photodynamic substances (for example, methylene blue) can be employed. Photodynamic substances, however, are considered contaminants when making a pharmaceutical preparation, and therefore must be removed.

These problems remained unsolved until the development of the present invention.

BRIEF SUMMARY OF THE INVENTION

In order to accomplish these and other objects, there are provided, in accordance with one aspect of the invention, methods of preparing a virus-safe biological material obtained from human blood, comprising exposing the biological material to pulsed ultraviolet laser radiation having energy in the range of about 0.1 to about 100 J/cm$^2$, wherein (i) the exposing is performed at a low temperature and in the absence of stabilizers, quenchers and photoactive substances, (ii) the virus-safe biological material is substantially free of denatured proteins. The source of the pulsed ultraviolet laser radiation can be a monochromatic laser. The energy of the laser can be less than 50 J/cm$^2$, and even less than 20 J/cm$^2$. The material can be, for example, human plasma or a human plasma fraction. The low temperature can be less than about 10° C., and can be, for example, about 4° C. to about 6° C.

In accordance with another aspect of the invention, there are provided methods of producing a virus-safe human plasma-derived product, comprising exposing human plasma or a human plasma fraction to pulsed ultraviolet laser radiation having energy in the range of about 0.1 to about 100 J/cm$^2$, wherein (i) the exposing is performed at a low temperature and in the absence of stabilizers, quenchers and photoactive substances, (ii) at least 70% of Factor VII or Factor X activity is preserved, (iii) the active virus titer is reduced at least about $10^4$, and (iv) the virus-safe human plasma-derived product is substantially free of denatured proteins, and purifying plasma proteins from the exposed human plasma or human plasma fraction. The plasma proteins can be, for example, coagulation factors, immunoglobulins, albumin and fibrinogen. The source of the pulsed ultraviolet laser radiation can be a monochromatic laser. The low temperature during exposure can be less than about 10° C., and can be, for example, about 4° C. to about 6° C.

In accordance with still another aspect of the invention, there are provided methods of treating human cells in a biological preparation, comprising exposing the human cells to pulsed ultraviolet laser radiation having energy in the range of about 0.1 to about 100 J/cm$^2$, wherein the exposing is performed at a low temperature and in the absence of stabilizers, quenchers and photoactive substances, wherein the exposing inactivates contaminating viruses in order to make the preparation virus-safe. The human cells can be, for example, bone marrow cells, red blood cells, white blood cells or stem cells. The low temperature can be less than about 10° C., and can be, for example, about 4° C. to about 6° C.

In accordance with yet another aspect of the invention, there are provided preparations comprising a virus-safe biological material from human blood, wherein the virus-safe biological material from human blood is obtainable by exposing the biological material to pulsed ultraviolet laser radiation having energy in the range of about 0.1 to about 100 J/cm$^2$, wherein (i) the exposing is performed at a low temperature and in the absence of stabilizers, quenchers and photoactive substances, (ii) the active virus titer is reduced at least about 10$^4$, and (iii) the virus-safe biological material is substantially free of denatured proteins. The source of the pulsed ultraviolet laser radiation can be a monochromatic laser. The energy of the laser can be less than 50 J/cm$^2$, and even less that 20 J/cm$^2$. The material can be, for example, human plasma or a human plasma fraction. The low temperature can be less than about 10° C., and can be, for example, about 4° C. to 6° C.

An object of the invention is to provide methods of producing virus-safe biological materials, such as cells and human blood derived products.

Another object of the invention is to provide virus-safe biological materials, such as cells and human blood derived products.

Another object of the invention is to provide virus-safe blood products while avoiding a substantial presence of denatured proteins.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Broadband (polychromatic) and narrow band (mono or nearly monochromatic) light sources are available offering a broad spectrum of potential applications. Monochromatic sources, however, have the advantage of allowing tailoring the light spectra to the properties of the targeted material. This approach leads to selective photon/molecule interactions and allows sparing other essential molecules in the host material.

Mercury lamp technology emits UV light in a continuous form and transfers energy to the targeted surface at relatively low average irradiance power (tens of mW/cm$^2$). Such lamps have demonstrated the ability of UV technology to achieve non-contact energy transfer and disinfection effects on a variety of materials.

Another mode of delivering UV energy is available due to the development of pulsed power sources, particularly through the utilization of laser technology. Contrary to the conventional, continuous, low power irradiance sources available with current mercury lamp technology, lasers allow the generation of extremely short duration pulses capable of illuminating surface and transferring energy in extremely high peak power (kW to MW).

The pulsed UV technology is different from the many industrial applications based upon conventional, current UV sources, (e.g., Hg lamps, *Ex lamps, etc.). The pulsed UV process is able to rapidly and irreversibly disrupt genetic mechanisms leading to cell division by altering irreversibly (non-repairable) the structural composition of the nucleic acids in bacteria and other microorganisms.

The invention provides a methodology for achieving virus-safe biological materials, such as cells, proteins and preparations obtained or derived from blood, blood constituents (for example, plasma), blood fractions (for example, plasma fractions), and bone marrow using pulsed UV light. Although UV light is effective against bacteria, protozoans and fungi as well as viruses, it is the viruses that are of the most importance in the context of the present invention. Nevertheless, inactivation and/or removal (partitioning) of bacteria, protozoans and fungi are within the scope of the present invention.

The phrase "virus-safe" refers to a materials that have been treated to inactivate and/or remove contaminating viruses such that administration of the material to a patient carries no more than a medically-acceptable risk of causing an infection in the patient. One useful demarcation for evaluating viral inactivation efficacy is to require the process to reduce active viral titer by about 10$^4$ or more. The invention also provides products obtainable by practice of the inventive methodologies.

The invention employs pulsed UV radiation that is of sufficient energy and duration to inactivate contaminating pathogens, including viruses, while minimizing denaturation of proteins of interest so that the resulting preparation yielded by practice of the method is substantially free of denatured proteins. For example, the pulsed ultraviolet laser radiation has energy in the range of about 0.1 to about 100 J/cm$^2$, although depending on the subject material that is being treated, energy levels can be outside of the above range. The above range serves as a useful referent, however.

The skilled person can recognize that a preparation is substantially free of denatured protein by, for example, determining the specific activity of the preparation of the protein of interest. The minimization of denaturation results in higher yields and lessens the purification burden. Guidance on this subject can be obtained by reference to the data contained herein.

One aspect responsible for the effective inactivation combined with minimization of denaturation is the use of a low temperature to conduct the process. A low temperature should be above the freezing temperature of the particular substance undergoing the inactivation methodology. The freezing point of water at standard pressure is 0° C., and provides a useful referent because most liquid biological materials are aqueous. The skilled person can adjust the low temperature for materials with freezing points that diverge from that of water. A "low temperature" is sufficiently close to the freezing point to minimize protein denaturation while permitting effective viral inactivation. Where a solution that freezes at about 0° C. is treated, the temperature employed preferably is less than about 10° C., but can be above this temperature. One useful range is about 4° C. to about 6° C. Thus, for example, in accordance with the teachings contained herein the skilled person could conduct the inactivation at 3.5° C., 7° C. or 12.5° C., for example, so long as the skilled person had conducted a simple process assessment, again in accordance with the teachings herein, before instituting large production runs.

The use of a monochromatic laser is an appropriate device to provide the pulsed ultraviolet radiation. Other devices capable of producing such radiation also can be employed according to the invention.

Practice of the invention avoids the need for photodynamic substances, like methylene blue, to effect inactivation. This capability means that the use of such substances is avoided, which simplifies the preparation, purification and finishing process.

The invention is further described by the following examples, which are illustrative of the invention but do not limit the invention in any manner.

EXAMPLE 1

ABILITY OF LASER TREATMENT TO INACTIVATE VIRUSES

The viruses studied herein appear to be quite sensitive to laser treatment as measured by their loss of infectivity in cell culture, even when very low doses of laser energy are used. For these experiments, viruses are grown in cell culture, harvested, and then suspended in either phosphate buffered saline (PBS) solution or in fetal bovine serum (FBS) before being given laser treatment at a variety of energy doses (expressed as joules or millijoules per $cm^2$) and at wavelengths of 248 nm or 308 nm. These laser treated virus solutions, along with non-laser treated control virus solutions, were then tested for their ability to infect and proliferate in cell culture as assessed by using a microtitration assay.

Microtitration assays measure the infectivity and concentration of virus and expresses the results in terms of a $TCID_{50}$ per ml (tissue culture infective dose per ml). Three different types of viruses have been tested:

(1) Bluetongue virus (BTV) which is a non-enveloped, double stranded RNA virus;

(2) Bovine viral diarrhea virus (BVDV) which is a non-enveloped, single stranded RNA virus; and (3) Infectious bovine rhinotracheitis virus (IBRV) which is an enveloped, double stranded DNA virus.

Bluetongue Virus (BTV)

Figure 1:
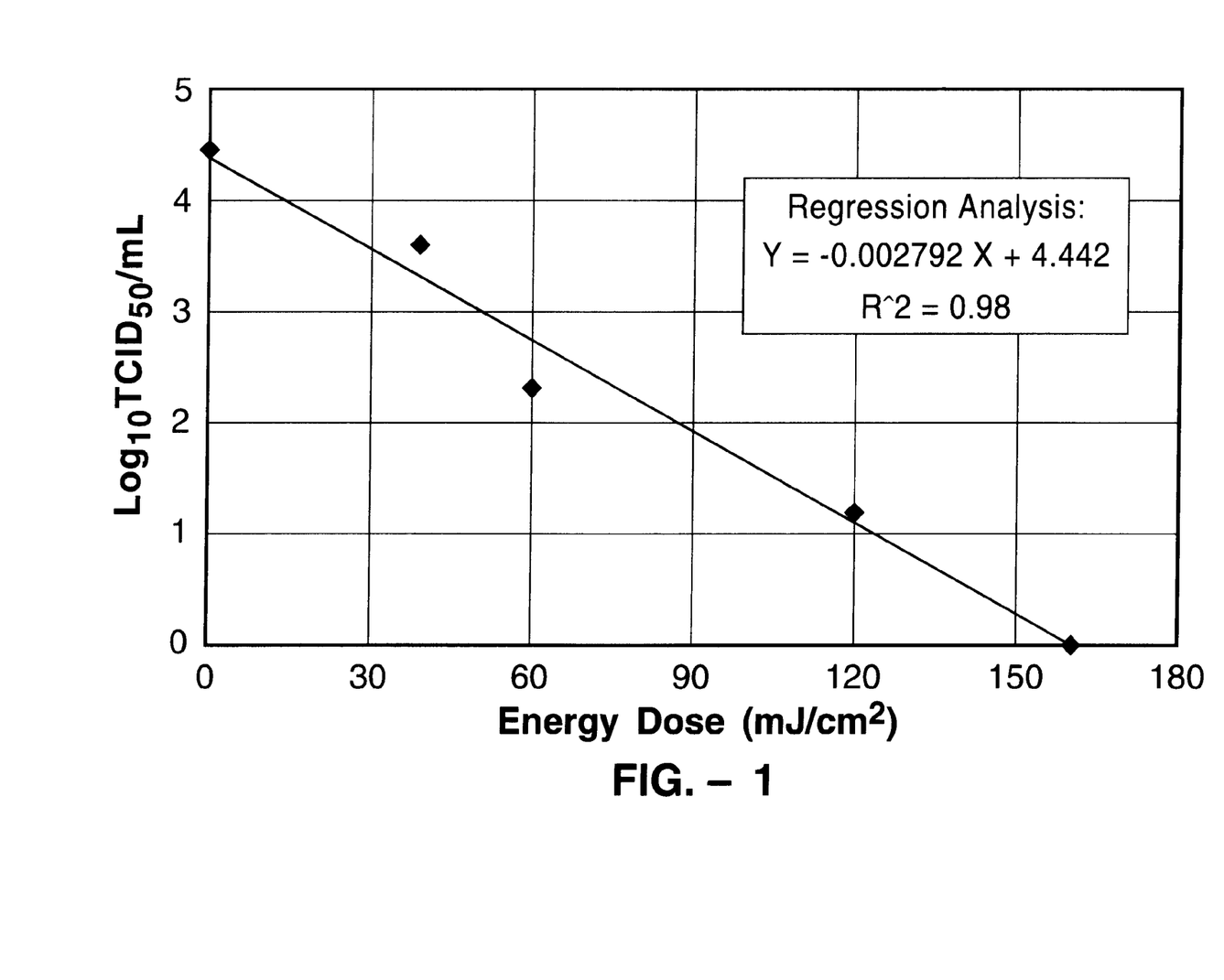
FIG. 1 is a graph depicting data from a pulsed UV light (248 nm) inactivation of BTV in PBS.

The results for an experiment using BTV suspended in PBS are shown in the Table 1 and FIG. 1.

These results show that using 248-nm UV light, very low UV dose in the mJ range (for example, as low as about 160 $mJ/cm^2$) were effective for a complete inactivation of BTV. At this dose, there was no detectable, infective virus present in the cell cultures using the microtitration assay. Control (untreated) virus solutions showed infectivity and destroyed the cell culture monolayer. These control solutions were determined to have titer of $10^{4.5}$ $TCID_{50}/ml$.

Pulsed UV doses as low as 40 $mJ/cm^2$ were able to reduce the infectivity of the virus ten-fold. FIG. 1 shows that there is a linear relationship between UV dose and virus inactivation. It also was calculated that about each 40 $mJ/cm^2$ increment results in 1 log (ten-fold) decrease in virus titer.

Figure 2:
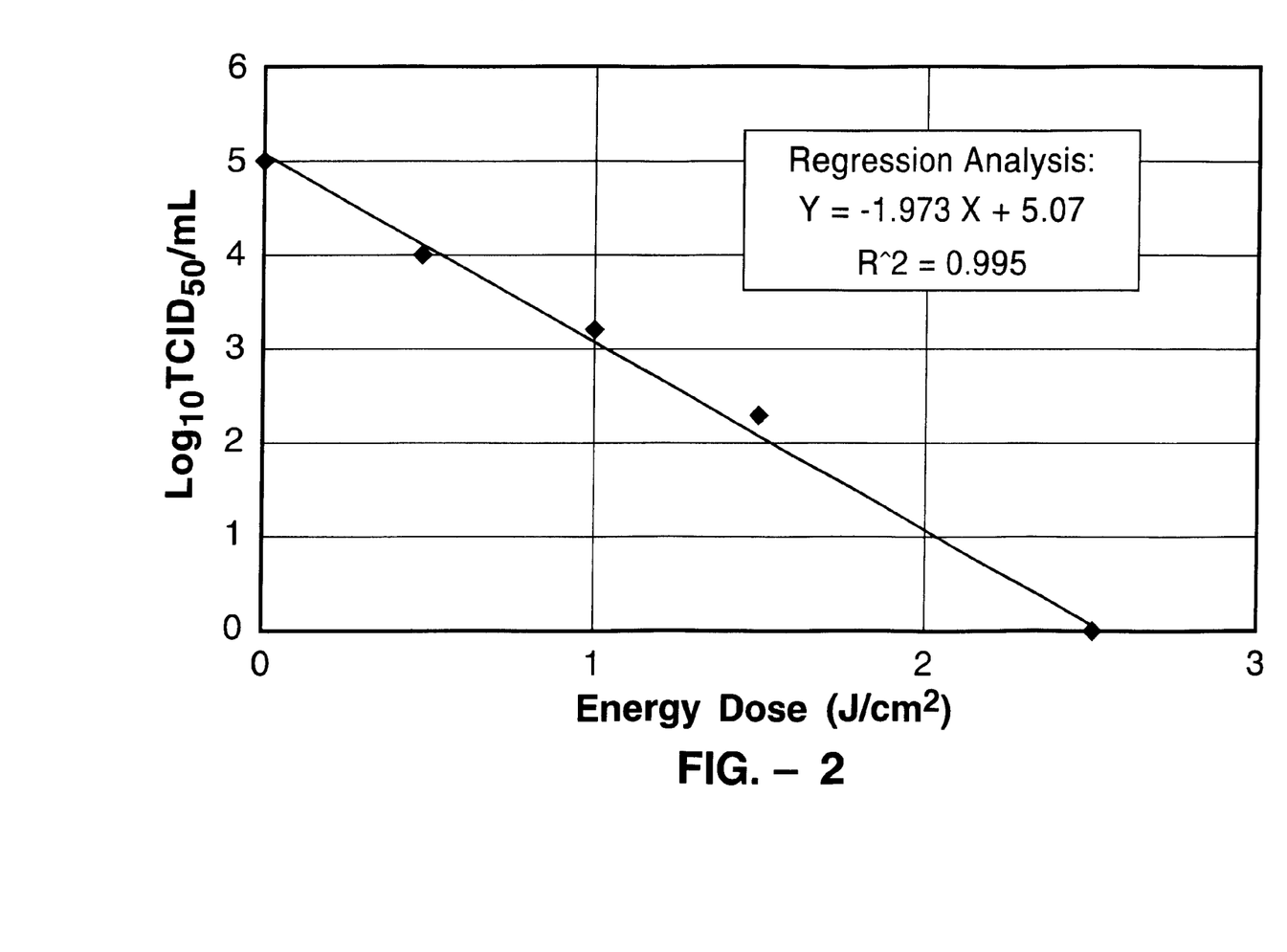
FIG. 2 is a graph depicting data from a pulsed UV light (248 nm) inactivation of BTV in FBS.

The results for an experiment using a BTV suspended in fetal bovine serum (FBS) are shown in Table 2 and FIG. 2.

A treatment dose as low as 2.5 $J/cm^2$ was sufficient to completely eliminate virus infectivity. There was no evidence of the presence of viable BTV in the cell cultures tested. The titer of non laser-treated virus controls was $10^{4.0}$ $TCID_{50}/ml$. For each increment in pulsed UV dose of 0.7 $J/cm^2$, there was a ten-fold decrease in the concentration of BTV.

Again, BTV suspended in FBS, appears to be quite sensitive to inactivation by laser treatment with 248 nm photons.

The pulsed UV dose at (248 nm) required to eliminate BTV from FBS, as compared to PBS, is 15 times greater. This difference is perhaps due to the optical properties of the host media (i.e. optical transparency). In PBS, the buffered saline media is an optically clear aqueous solution, whereas fetal bovine serum is a less transparent, complex colored solution which contains UV absorbent chemicals, such as proteins, which do absorb some of the 248 nm UV light energy. Nevertheless, the pulsed UV dose at 248 nm for BTV inactivation suspended in PBS or FBS is low (<3 $J/cm^2$). With this UV energy level and because the UV photons are in resonance with the genetic material, most other molecules are spared and little if any detectable damage occurs.

Using UV photons at 308 nm produced with the same excimer laser technique, similar experiments were conducted. It was demonstrated that 308 nm UV photons were less effective to inactivate BTV as compared to the use of 248 nm UV photons. Higher UV doses were required to achieve similar inactivation levels when using the 308 nm UV photons.

When BTV was suspended in PBS, a 5.0 $J/cm^2$ UV dose at (308 nm) resulted in a 1000-fold decrease in virus titer using the microtitration assay. When BTV was suspended in FBS, a 10.0 $J/cm^2$ UV dose (308 nm) caused a 10-fold reduction in virus infectivity. However, complete virus inactivation was not achieved with the range of UV doses tested in this experiment (up to 10 $J/cm^2$).

Bovine Viral Diarrhea Virus (BVDV)

The ability of laser treatment at a wavelength of 248 nm to inactivate BVDV suspended in PBS or FBS also was demonstrated. Treating with a UV dose at (248 nm) of 3 $J/cm^2$ completely destroyed virus infectivity as shown when assayed in cell cultures. The titer for untreated controls was $10^{4.4}$ $TCID_{50}/ml$ for BVDV suspended in PBS and FBS, as determined with the microtitration assay.

Using 308 nm UV light, a UV dose of 10.0 $J/cm^2$ resulted in complete virus inactivation for BVDV suspended in PBS. For BVDV suspended in FBS, complete virus inactivation was achieved with an energy dose of 40 $J/cm^2$ at 308 nm UV light.

Infectious Bovine Rhinotracheitis virus (IBRV)

Figure 3:
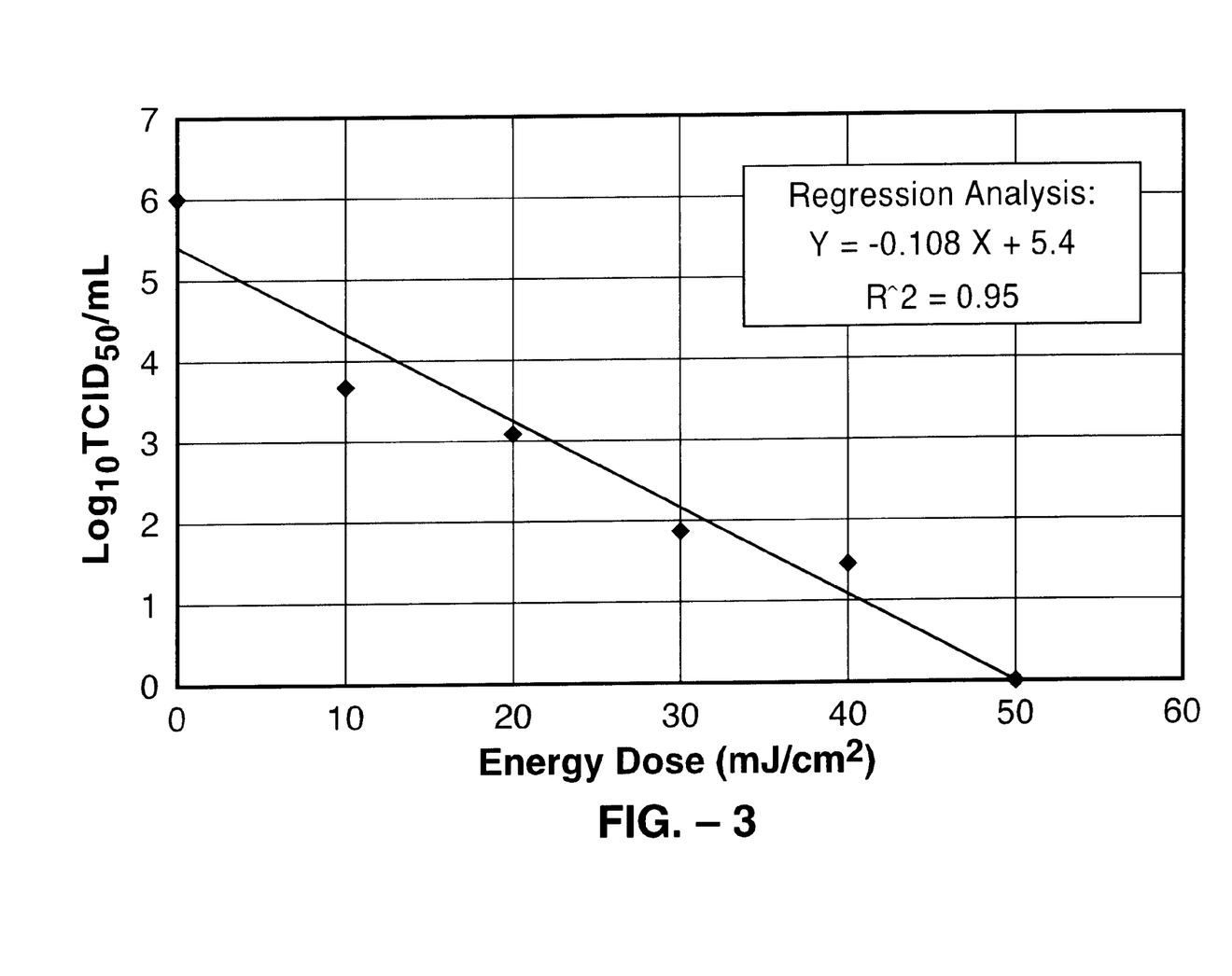
FIG. 3 is a graph depicting data from a pulsed UV light (248 nm) inactivation of IBRV in PBS.

Using the 248 nm laser, IBRV diluted in PBS was completely inactivated at an energy dose as low as 50 $mJ/cm^2$ (see FIG. 3). The untreated control IBRV solution had a virus titer of $10^6$ $TCID_{50}/ml$. Thus, this laser treatment resulted in a 1,000,000 fold reduction in the IBRV activity.

EXAMPLE 2

FUNCTIONALITY OF PULSED UV TREATED FBS ASSAYED BY CELL CULTURE GROWTH

Fetal bovine serum (FBS) is an essential additive to culture medium in order to support the growth of a variety of cell cultures, in vitro, including those used to generate other cell products of pharmacological significance and for vaccine production. It contains proteins, carbohydrates, vitamins, hormones and other components which have not yet been fully characterized. Many types of cell cultures are unable to grow in the absence of FBS. There is the concern, however, that since FBS is bovine-derived, it may contain undetectable amounts of bovine viruses which could be unknowingly introduced into cell culture and then can grow and proliferate.

Preliminary experiments have shown that exposure of FBS to excimer laser generated UV photons (248, 308 nm) eliminates viral contamination. Exposure to UV light may possibly photolyze (damage) some of the UV absorbent components and, therefore, affect the ability of FBS to support cellular growth.

Experiments were conducted in which FBS was exposed to a larger UV dose than needed for viral inactivation (for example, 10.0 J/cm$^2$ at 248 nm). The overexposed FBS was then used as an additive to cell culture media which was then used to grow four different cell lines.

Pulsed UV treated (overexposed, 10 J/cm$^2$) FBS and untreated FBS were compared to measure their ability to support cell culture growth. Tests included total cell and viable cell counts. The cell lines were maintained for at least 14 passages over a 2 month period. Cell lines tested were BHK-21 (Baby Hamster Kidney Cells), Vero (African Green Monkey Kidney Cells), myeloma cells (p3X63Ag8.653 murine myeloma cells) and SF-9 (an insect cell line). The results of these experiments for all cell lines tested were as follows:

(1) There was no difference in total cell counts, with cells being grown in culture medium containing laser treated and untreated FBS. Cell counts using treated FBS were 98–99% of the cells counts grown with untreated FBS.

(2) There was little difference in the viability for cells grown in medium containing treated and untreated FBS. Cell counts averaged 95% of those for the control cell lines.

The results summarized above are given in Tables 3 to 9, reproduced below.

The data demonstrate that pulsed UV treatment of FBS (248 nm) can be an effective method to provide a cell culture media free of viral contamination. Furthermore, the photochemical process was shown to be effective for altering the virus genetic material (targeted material) without inducing, directly or indirectly, detectable damage in non-targeted materials as assessed by its biological activity.

Finally, in a separate experiment, and to further evaluate the health of cells to support viral replication, one of the cell lines (BHK) was intentionally infected with BTV. It was found that the cells grown in culture medium containing laser treated FBS supported BTV replication as well as the cells grown in medium with control untreated FBS.

EXAMPLE 3

PULSED UV (PUV) EFFECT ON PROTEINS

Pulsed UV light induces an inhibitory effect on cell division mechanisms which eventually leads to microbial death. The new process is carried out in extremely short duration pulses (picoseconds to nanoseconds) which transfer photon energy selectively, via the resonance phenomena, to the targeted nucleic acids. The energy intensity (UV dose) is rather low (100's of mJ/pulse) so as to minimize or prevent any unwanted sensory change in the subject material undergoing treatment. This is accomplished by using extremely short duration pulses (picoseconds to nanoseconds) so that the resulting photon energy transfer process operates with extremely high peak (instant) power (megawatts). Under these conditions, pathogens are not capable of repairing the induced UV damage to their essential genetic materials (DNA and/or RNA) and are unable to survive the high power UV energy input process. Therefore, under pulsed UV power conditions with the appropriate energy inputs (dose) no surviving pathogen remains, thereby eliminating the probability for mutations. Results attained with pulsed UV on certain proteins is set forth in Table 10.

Although the description above contains many specificities, these should not be construed as limiting the scope of the invention but as merely providing illustrations of some of the presently preferred embodiments of this invention. Thus the scope of this invention should be determined by the appended claims and their legal equivalents.

TABLE 1

Effect of Laser Treatment at 248 nm on BTV in PBS as Determined by the Decrease in Titer Using the Microtiter Assay.

| Treatment Procedure | Titer of the Virus (TCID$_{50}$/ml) |
|---|---|
| Untreated (1:6 dilution) | $10^{4.5}$ |
| Treated with Laser | |
| 36 mJ/cm$^2$ | $10^{5.85}$ |
| 72 mJ/cm$^2$ | $10^{2.3}$ |
| 120 mJ/cm$^2$ | $10^{1.3}$ |
| 156 mJ/cm$^2$ | 0 |
| 204 mJ/cm$^2$ | 0 |
| 240 mJ/cm$^2$ | 0 |
| 276 mJ/cm$^2$ | 0 |
| 324 mJ/cm$^2$ | 0 |

TABLE 2

Effect of Laser Treatment at 248 nm on BTV in PBS as Determined by the Decrease in Titer Using the Microtitration Assay.

| Treatment Procedure | Titer of the Virus (TCID*/ |
|---|---|
| Untreated (1:6 dilution) | $10^{4.5}$ |
| Treated with Laser | |
| 0.55 J/cm$^2$ | $10^{4.0}$ |
| .99 J/cm$^2$ | $10^{3.3}$ |
| 1.54 J/cm$^2$ | $10^{2.5}$ |
| 1.98 J/cm$^2$ | 0 |
| 2.65 J/cm$^2$ | 0 |
| 2.97 J/cm$^2$ | 0 |
| 3.52 J/cm$^2$ | 0 |
| 3.96 J/cm$^2$ | 0 |
| 4.51 J/cm$^2$ | 0 |

TABLE 3

Summary of Average of Cell Counts for BHK-21, Vero, Myeloma and S1-9 Cell Lines Grown on Medium with Laser Treated (10 J/cm$^2$) or Untreated FBS.

| Cell Line | BHK-21 | Vero | Myeloma | SF-9 |
|---|---|---|---|---|
| Number of Passages | 14 | 14 | 16 | 18 |
| Laser Treated FBS (10 J/cm$^2$) | | | | |
| Average of Viable Cells/ml *(×10$^6$) | 1.28 | 2.66 | 2.83 | 4.92 |
| Average of Total Cells/ml *(×10$^6$) | 1.32 | 2.74 | 3.48 | 6.38 |
| % Viability | 97 | 97 | 81 | 77 |
| Untreated FBS | | | | |
| Average of Viable Cells/ml *(×10$^6$) | 1.30 | 2.67 | 3.12 | 5.20 |
| Average of Total Cells/ml *(×10$^6$) | 1.34 | 2.78 | 3.54 | 6.50 |
| % Viability | 97 | 96 | 89 | 80 |

TABLE 4

Summary of Growth Promotion of Cell Lines Grown on Medium with Laser-Treated (10 J/cm$^2$) FBS Compared with Cell Lines Grown on Medium with Untreated FBS (Control).

| | Growth Promotion (% of Control) | | | |
|---|---|---|---|---|
| Cell Line | BHK-21 | Vero | Myeloma | SF-9 |
| Viable Cells | 98 | 99 | 91 | 95 |
| Total Cells | 98 | 98 | 99 | 98 |

TABLE 5

Titer Comparison of the BTV-10 Produced on Vero Cells Grown on Medium with Laser Treated (10 J/cm$^2$) or Untreated FBS at the Passage Level 15.

| | Vero Cells Grown on | |
|---|---|---|
| | Laser-treated FBS (10 J/cm$^2$) | Untreated FBS (Controls) |
| Titer of the Virus (log$_{10}$TCID$_{50}$/ml) | 6.88 | 6.80 |

TABLE 6

Cell Counts for BHK-21 on Medium with Laser Treated (10 J/cm$^2$) FBS and Untreated FBS, Medium: MEM + 10% FBS + 5% Tryptose Phosphate + 1% L-Glutamine + 1% P/S.

| | Passage Level | | | | | | | |
|---|---|---|---|---|---|---|---|---|
| | 1 | 2 | 3 | 4 | 5 | 6 | 7 | 8 |
| Laser Treated FBS (10 J/cm$^2$) | | | | | | | | |
| Average[1] of Viable Cells/ml (× 10$^6$) | | 1.3 | 0.98 | 0.98 | 1.16 | 1.25 | 1.3 | 1.45 |
| Average of Total Cells/ml (× 10$^6$) | | 1.34 | 1.01 | 1.02 | 1.2 | 1.3 | 1.34 | 1.46 |
| % Viability | | 97 | 96 | 96 | 98 | 96 | 97 | 99 |
| Untreated FBS | | | | | | | | |
| Average*[1] of Viable Cells/ml (× 10$^6$) | | 1.67 | 1.12 | 0.91 | 1.2 | 1.06 | 1.48 | 1.42 |
| Average of Total Cells/ml (× 10$^6$) | | 1.74 | 1.15 | 0.92 | 1.24 | 101 | 1.5 | 1.44 |
| % Viability | | 95 | 96 | 97 | 97 | 96 | 95 | 97 |

| | Passage Level | | | | | | |
|---|---|---|---|---|---|---|---|
| | 9 | 10 | 11 | 12 | 13 | 14 | 15 |
| Laser Treated FBS (10 J/cm$^2$) | | | | | | | |
| Average of Viable Cells/ml (× 10$^2$) | 1.3 | 1.4 | 1.76 | 1.25 | 1.31 | 1.2 | 1.38 |
| Average of Total Cells/ml (× 10$^5$) | 1.36 | 1.46 | 1.83 | 1.27 | 1.34 | 1.24 | 1.42 |
| % Viability | 95 | 96 | 96 | 98 | 98 | 96.6 | 95 |
| Untreated FBS | | | | | | | |
| Average of Viable Cells/ml (× 10$^2$) | 1.34 | 1.7 | 1.5 | 1.28 | 1.24 | 1.19 | 1.4 |
| Average of Total Cells/ml (× 10$^5$) | 1.38 | 1.72 | 1.53 | 1.29 | 1.28 | 1.23 | 1.44 |
| % Viability | 96 | 98 | 99 | 99 | 97 | 96 | 97 |

TABLE 7

Cell Counts for Vero Cells on Medium with Laser Treated (10 J/cm$^2$) FBS and Untreated FBS, Medium: MEM + 10% FBS + 5% Tryptose Phosphate + 1% *L-Glutamine + 1% P/S.

| | Passage Level | | | | | | | |
|---|---|---|---|---|---|---|---|---|
| | 1 | 2 | 3 | 4 | 5 | 6 | 7 | 8 |
| Laser Treated FBS (10 J/cm$^2$) | | | | | | | | |
| Average*[1] of Viable Cells/ml (× 10$^6$) | | 1.63 | 2.58 | 2.29 | 2.8 | 2.58 | 2.79 | 2.86 |
| Average of Total Cells/ml (× 10$^6$) | | 1.66 | 2.64 | 2.3 | 2.9 | 2.62 | 2.9 | 2.98 |
| % Viability | | 98 | 97 | 98 | 97 | 98 | 95 | 95 |
| Untreated FBS | | | | | | | | |
| Average*[1] of Viable Cells/ml (× 10$^6$) | | 1.77 | 2.12 | 2.64 | 2.7 | 2.5 | 2.8 | 2.48 |
| Average of Total Cells/ml (× 10$^6$) | | 1.77 | 2.17 | 2.76 | 2.8 | 2.6 | 2.98 | 2.8 |
| % Viability | | 98 | 97 | 96 | 97 | 96 | 96 | 95 |

| | Passage Level | | | | | | |
|---|---|---|---|---|---|---|---|
| | 9 | 10 | 11 | 12 | 13 | 14 | 15 |
| Laser Treated FBS (10 J/cm$^2$) | | | | | | | |
| Average*[1] of Viable Cells/ml (× 10$^6$) | 3.56 | 2.76 | 2.2 | 3.09 | 3.34 | 2.72 | 2.04 |
| Average of Total Cells/ml (× 10$^6$) | 3.8 | 2.84 | 2.29 | 3.19 | 3.46 | 2.79 | 2.08 |
| % Viability | 94 | 97 | 96 | 96 | 96 | 97 | 98 |
| Untreated FBS | | | | | | | |
| Average*[1] of | 3.42 | 2.2 | 3.24 | 2.86 | 3.18 | 2.8 | 2.76 |

TABLE 7-continued

Cell Counts for Vero Cells on Medium with Laser Treated (10 J/cm$^2$) FBS and Untreated FBS, Medium: MEM + 10% FBS + 5% Tryptose Phosphate + 1% *L-Glutamine + 1% P/S.

| Viable Cells/ml (× 10$^6$) | | | | | | | |
|---|---|---|---|---|---|---|---|
| Average of Total Cells/ml (× 10$^6$) | 3.58 | 2.3 | 3.37 | 3.03 | 3.36 | 2.9 | 2.82 |
| % Viability | 96 | 95 | 96 | 94 | 94 | 96 | 97 |

*[1]Average of three flasks.

TABLE 8

Cell Counts for Myeloma Cells on Medium with Laser Treated (10 J/cm$^2$) FBS and Untreated FBS, Medium: RPMI + 10% FBS + 1% P/S +1% non-essential amino acids + 1% Sodium Pyruvate + 1% L-Glutamine.

| | Passage Level | | | | | | | |
|---|---|---|---|---|---|---|---|---|
| | 1 | 2 | 3 | 4 | 5 | 6 | 7 | 8 |
| Laser Treated FBS (10 J/cm$^2$) | | | | | | | | |
| Average*[1] of Viable Cells/ml (× 10$^6$) | 2.08 | 3.5 | 2.12 | 2.54 | 3.02 | 2.48 | 2.48 | |
| Average of Total Cells/ml (× 10$^6$) | 2.68 | 4.28 | 2.36 | 3.18 | 3.62 | 2.76 | 2.65 | |
| % Viability | 76 | 84 | 89 | 81 | 83 | 80 | 90 | |
| Untreated FBS | | | | | | | | |
| Average*[1] of Viable Cells/ml (× 10$^6$) | 2.19 | 4.2 | 2.2 | 2.82 | 3.72 | 2.43 | 2.8 | |
| Average of Total Cells/ml (× 10$^6$) | 2.62 | 4.7 | 2.4 | 3.24 | 4.1 | 2.73 | 2.77 | |
| % Viability | 82 | 89 | 90 | 89 | 89 | 88 | 95 | |

| | Passage Level | | | | | | |
|---|---|---|---|---|---|---|---|
| | 9 | 10 | 11 | 12 | 13 | 14 | 15 |
| Laser Treated FBS (10 J/cm$^2$) | | | | | | | |
| Average*[1] of Viable Cells/ml (× 10$^6$) | 4.5 | 2.3 | 3.54 | 3.1 | 3.04 | 2.76 | 3.28 |
| Average of Total Cells/ml (× 10$^6$) | 5.7 | 2.62 | 4.2 | 3.6 | 3.88 | 4.18 | 3.9 |
| % Viability | 79 | 88 | 84 | 86 | 78 | 66 | 84 |

TABLE 8-continued

Cell Counts for Myeloma Cells on Medium with Laser Treated (10 J/cm$^2$) FBS and Untreated FBS, Medium: RPMI + 10% FBS + 1% P/S +1% non-essential amino acids + 1% Sodium Pyruvate + 1% L-Glutamine.

| Untreated FBS | | | | | | | |
|---|---|---|---|---|---|---|---|
| Average*[1] of Viable Cells/ml (× 10$^6$) | 4.6 | 2.8 | 3.9 | 3.08 | 3.7 | 3.08 | 2.9 |
| Average of Total Cells/ml (× 10$^6$) | 2.1 | 3.1 | 4.15 | 3.5 | 4.26 | 4.3 | 3.42 |
| % Viability | 88 | 92 | 93 | 88 | 89 | 71 | 84 |

| | Passage Level | |
|---|---|---|
| | 16 | 17 |
| Laser Treated FBS (10 J/cm$^2$) | | |
| Average*[1] of Viable Cells/ml (× 10$^6$) | 2.78 | 1.78 |
| Average of Total Cells/ml (× 10$^6$) | 3.89 | 2.26 |
| % Viability | 71 | 78 |
| Untreated FBS | | |
| Average*[1] of Viable Cells/ml (× 10$^6$) | 3.9 | 1.72 |
| Average of Total Cells/ml (× 10$^6$) | 4.5 | 1.9 |
| % Viability | 86 | 90 |

TABLE 9

Cell Counts for SF-9 Cells on Medium with Laser Treated (10 J/cm$^2$) FBS and Untreated FBS, Medium: Grace's Insect Medium with L-Glutamine (TNM-FM medium) (Gibco Co.) + 0.2% Gantamycin + 10% FBS.

| | Passage Level | | | | | | | |
|---|---|---|---|---|---|---|---|---|
| | 1 | 2 | 3 | 4 | 5 | 6 | 7 | 8 |
| Laser Treated FBS (10 J/cm$^2$) | | | | | | | | |
| Average*[1] of Viable Cells/ml (× 10$^6$) | | 3.7 | 4.05 | 5.92 | 5.74 | 6.02 | 5.66 | 5.1 |
| Average of Total Cells/ml (× 10$^6$) | | 5.64 | 5.8 | 7.8 | 7.4 | 8.18 | 7.3 | 6.89 |
| % Viability | | 65 | 72 | 75 | 77 | 73 | 77 | 74 |
| Untreated FBS | | | | | | | | |
| Average*[1] of Viable Cells/ml (× 10$^6$) | | 3.84 | 3.6 | 4.8 | 5.94 | 5.7 | 5.2 | 4.7 |
| Average of Total Cells/ml (× 10$^6$) | | 6.8 | 5.15 | 6.3 | 7.76 | 7.3 | 6.48 | 6.4 |
| % Viability | | 68 | 70 | 76 | 76 | 78 | 80 | 73 |

| | Passage Level | | | | | | |
|---|---|---|---|---|---|---|---|
| | 9 | 10 | 11 | 12 | 13 | 14 | 15 |
| Laser Treated FBS (10 J/cm$^2$) | | | | | | | |
| Average*[1] of Viable Cells/ml (× 10$^6$) | 6.8 | 3.9 | 3.68 | 6.96 | 3.5 | 7.02 | 6.0 |
| Average of Total Cells/ml (× 10$^6$) | 7.9 | 5.4 | 6.3 | 7.6 | 4.0 | 8.7 | 7.16 |
| % Viability | 73 | 72 | 69 | 78 | 75 | 80 | 83 |

TABLE 9-continued

Cell Counts for SF-9 Cells on Medium with Laser Treated (10 J/cm$^2$) FBS and Untreated FBS, Medium: Grace's Insect Medium with L-Glutamine (TNM-FM medium) (Gibco Co.) + 0.2% Gantamycin + 10% FBS.

Untreated FBS

| | | | | | | | |
|---|---|---|---|---|---|---|---|
| Average*$^1$ of Viable Cells/ml (× 10$^6$) | 6.32 | 3.3 | 4.78 | 5.84 | 4.28 | 5.96 | 6.5 |
| Average of Total Cells/ml (× 10$^6$) | 8.28 | 4.5 | 6.62 | 7.14 | 5.58 | 6.9 | 8.02 |
| % Viability | 76 | 73 | 72 | 81 | 76 | 85 | 81 |

*$^1$Average of three flasks.

TABLE 10

Pulsed Laser Treated Samples

A = 248 nm Energy (J/cm$^2$)

| | | | Control (0) | .02 | .05 | 1 | 3 | 7 | 20 |
|---|---|---|---|---|---|---|---|---|---|
| | | | | | % of untreated | | | | |
| Plasma | #46154 70 mg/ml | Factor VII | =100 | n.o. | 85 | n.d. | 80 | n.d. | 26 |
| | | VWF.CBA | =100 | n.d. | 97 | n.d. | 87 | n.d. | 24 |
| | | Factor II | =100 | 100 | 88 | 91 | 88 | 80 | 40 |
| | | Factor VII | =100 | 99 | 94 | 88 | 76 | 56 | 23 |
| | | Factor IX | =100 | 104 | 102 | 98 | 87 | 60 | 24 |
| | | Factor X | =100 | n.d. | 86 | n.d. | 86 | n.d. | 32 |
| | | Protein C | =100 | 103 | 103 | 94 | 128.7 | 80 | 24 |
| Cyrosupernatant | KRf1698 65 mg/ml | Factor II | =100 | 93 | 95 | 88 | 73 | 73 | 37 |
| | | Factor VII | =100 | 68 | 92 | 92 | 78 | 102.7 | 53 |
| | | Factor IX | =100 | 104 | 98 | 87 | 85 | 88 | 25 |
| | | Factor X | =100 | n.d. | 94 | n.d. | 84 | n.d. | 32 |
| | | Protein C | =100 | 83 | 94 | 96 | 96 | 76 | 32 |
| DEAE-Eluate | F9A40198 15 mg/ml | FEIBA | =100 | n.d. | 81 | n.d. | 24 | n.d. | <1 |
| | | Factor II | =100 | 122 | 90 | 87 | 85 | 17 | 5 |
| | | Factor VII | =100 | 91 | 85 | 74 | 38 | 6 | 0.1 |
| | | Factor IX | =100 | 95 | 82 | 70 | 38 | 9 | 0.3 |
| | | Factor X | =100 | n.d. | 53 | n.d. | 66 | n.d. | 3 |
| | | Protein | =100 | 118 | 90 | 96 | 67 | 26 | 3 |
| FVIII-Eluate A | #B439198 0.3 mg/ml without albumin | Factor VII | =100 | n.d. | 4 | n.d. | 1 | n.d. | 0.1 |
| | | WWF:CBA | =100 | n.d. | 15 | n.d. | <4 | n.d. | <4 |
| FVIII-Eluate B | #B439198 1.2 mg/ml without albumin | Factor VII | =100 | n.d. | 14 | n.d. | 0.2 | n.d. | <0.1 |
| | | WWF:CBA | =100 | n.d. | 25 | n.d. | <3 | n.d. | <3 |

What is claimed is:

1. A method for preparing a virus-safe biological material obtained from human blood, comprising the steps of exposing a biological material to 248 nm pulsed ultraviolet laser radiation having an energy in the range of approximately 0.1 to 100 J/cm$^2$, wherein said exposure is performed at a material temperature of 12.5° C. or less, and wherein the active virus titer is reduced at least 10$^4$.

2. A method as recited in claim 1, wherein said biological material comprises human plasma material or a human plasma fraction material having Factor VIII or Factor X activity.

3. A method as recited in claim 2, wherein at least 70% of Factor VIII or Factor X activity is preserved.

4. A method as recited in claim 2, further comprising purifying plasma proteins from the exposed human plasma or plasma fraction.

5. A method for producing a virus-safe human plasma-derived product, comprising the steps of:

(a) exposing human plasma material or a human plasma fraction material having Factor VIII or Factor X activity to 248 nm pulsed ultraviolet laser radiation having an energy in the range of approximately 0.1 to 100 J/cm$^2$, wherein said exposure is performed at a material temperature of 12.5° C. or less, wherein at least 70% of Factor VIII or Factor X activity is preserved, and wherein the active virus titer is reduced at least 10$^4$; and (b) purifying plasma proteins from the exposed human plasma or plasma fraction.

6. A method as recited in claim 5, wherein said plasma proteins are selected from the group consisting of coagulation factors, immunoglobulins, albumin and fibrinogen.

7. A method for treating human cells in a biological preparation, comprising the steps of exposing said cells to 248 nm pulsed ultraviolet laser radiation having an energy in the range of approximately 0.1 to 100 J/cm$^2$, wherein said exposure is performed at a cell temperature of 12.5° C. or less, and wherein said exposure inactivates contaminating viruses.

8. A method as recited in claim 7, wherein said human cells are selected from the group consisting of bone marrow cells, red blood cells, white blood cells, and stem cells.

* * * * *